United States Patent [19]

Heine et al.

[11] 4,211,215
[45] Jul. 8, 1980

[54] ENDOSCOPE HOUSING COVER HINGE CONSTRUCTION UTILIZING A SPRING, BALL AND BORE ARRANGEMENT IN COMBINATION WITH A HINGE PIN

[75] Inventors: Helmut A. Heine, Herrsching; Helmut W. Rosenbusch, Weilheim; Otto H. Schmidt, Herrsching, all of Fed. Rep. of Germany

[73] Assignee: Heine Optotechnik GmbH & Co. KG., Herrsching, Fed. Rep. of Germany

[21] Appl. No.: 925,774

[22] Filed: Jul. 18, 1978

[30] Foreign Application Priority Data

Aug. 24, 1977 [DE] Fed. Rep. of Germany ....... 2738203

[51] Int. Cl.$^2$ .............................................. A61B 1/00
[52] U.S. Cl. ........................................................ 128/4
[58] Field of Search ........................................ 128/3–9, 128/10–13, 15–18; 16/158, 139, 145, 146, 171, 176, 177, 169, 191; 215/235–238, 243; 220/335, 343; 292/251

[56] References Cited

U.S. PATENT DOCUMENTS

| 263,448 | 8/1882 | Withey | 292/251 |
| 3,044,461 | 7/1962 | Murdock | 128/4 |
| 3,417,746 | 12/1968 | Moore et al. | 128/6 |

FOREIGN PATENT DOCUMENTS

| 272887 | 7/1969 | Austria | 16/169 |
| 1566179 | 5/1967 | Fed. Rep. of Germany | 128/6 |
| 17049 | of 1914 | United Kingdom | 128/4 |

*Primary Examiner*—Robert W. Michell
*Assistant Examiner*—Jeffrey W. Tayon
*Attorney, Agent, or Firm*—Woodcock, Washburn, Kurtz, Mackiewicz & Norris

[57] ABSTRACT

The invention discloses an endoscope, and particularly a rectoscope, having an improved means of securing a cover to the head housing of the endoscope using a releasable hinge. In a preferred embodiment a pin removably located in a bore forms the hinge for the cover connection.

6 Claims, 6 Drawing Figures

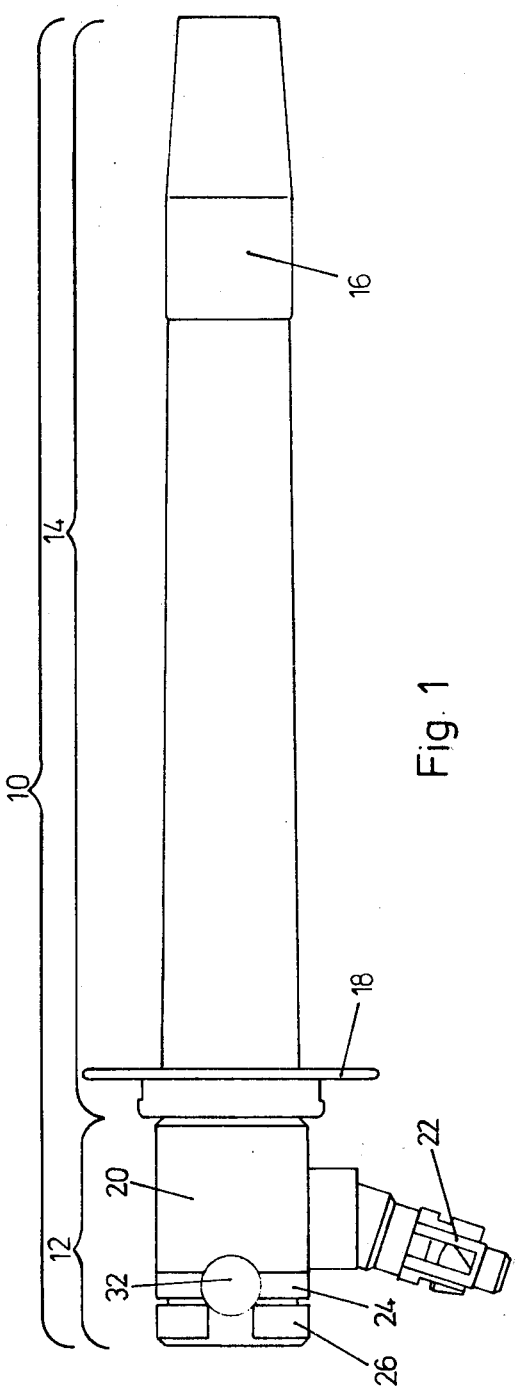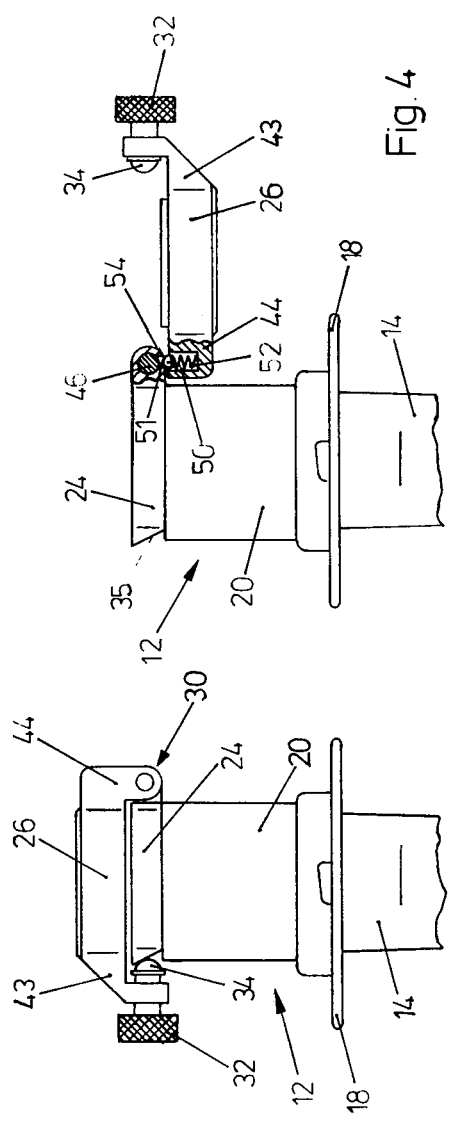

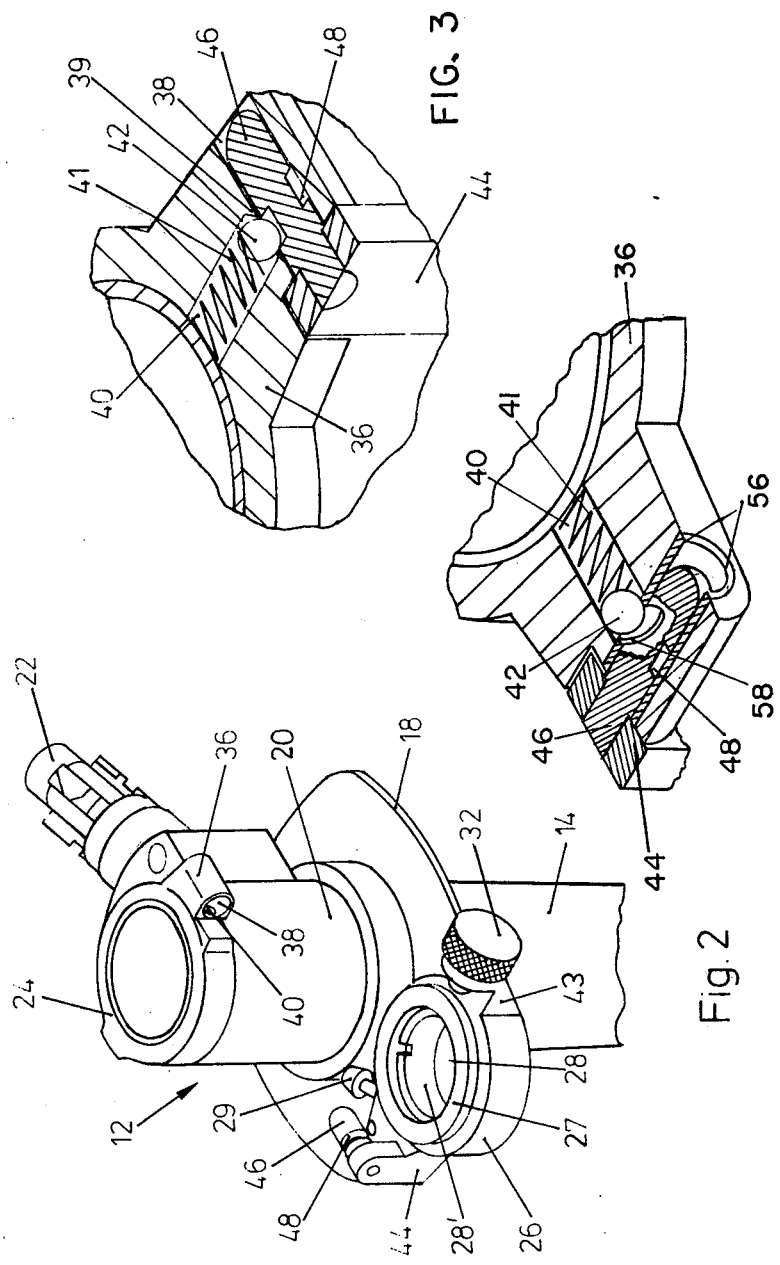

ENDOSCOPE HOUSING COVER HINGE CONSTRUCTION UTILIZING A SPRING, BALL AND BORE ARRANGEMENT IN COMBINATION WITH A HINGE PIN

BACKGROUND OF THE INVENTION

The invention relates to an endoscope, especially to a rectoscope, wherein connected to a tube there is a head, the housing of which can be closed at the end opposite the tube by means of a detachable cover with a window.

When examining an internal organ by means of an endoscope, thus the rectum in the case of a rectoscope, the rectoscope is first introduced into the rectum, the distal opening of the tube being closed by means of an obturator. After the sphincter has been overcome, the obturator is removed by pulling on its handle, which projects out of the open end on the opposite side to the tube. After this, the rectoscope is introduced as far as desired, by sight. Then the examination of the rectum can begin, the rectoscope normally being withdrawn gradually from the rectum as this is observed.

In order to enable an examination to be carried out when the rectum has been emptied (in this condition the internal walls of the rectum lie touching each other), it must be blown up slightly so that the inner walls become visible. For this purpose, the end of the head housing opposite to the tube can be closed with the aid of the cover so that the compressed air introduced into the rectoscope cannot escape. A connecting fixture fitted on the cover or on the housing of the head is used for the supply of compressed air.

It is clear that the proximal end of the head housing has to be opened and closed as quickly and simply as possible. In the rectoscope described above and disclosed in the published German specification AS-PS 1566 179, on both the cover and the head housing there are complementary surfaces in the shape of a truncated cone so that the cover only needs to be inserted in or withdrawn from the head housing. However, this kind of fixing of the cover on the head housing has the disadvantage that the connection between the cover and the head housing can easily become unsealed as the endoscope is manipulated, and may fall out under the increased internal pressure. In addition, production costs for making the complementary truncated cone surfaces are relatively high. These costs become unacceptably high when supplementary apparatus, such as a camera, for instance, is to be attached to the proximal end of the rectoscope. In this case, either an additional adaptor has to be provided or a truncated cone complementary surface has to be provided at the appropriate point on the supplementary apparatus as well. Moreover, the jerky movements when the cover is put on and taken off are painful for the patient.

In another known rectoscope the cover is attached pivotably and permanently to the head of the housing by means of a hinge. Since the cover cannot be taken off it is always a nuisance when it is not actually in use, for example, when the rectoscope is being introduced into the rectum, or when supplementary apparatus is connected, particularly if the connecting fixture for connecting up a blower is attached to it.

SUMMARY OF THE INVENTION

The invention is therefore based on the task of producing an endoscope, especially a rectoscope, in which the disadvantages and failings of the prior art are eliminated. In particular, the endoscope, especially a rectoscope, should be designed in such a way that with the simplest possible construction the cover can be opened and closed as rapidly as possible, and completely removed as easily as possible.

This task is solved according to the invention by attaching the cover to the housing of the head by means of a releasable hinge.

Since in the endoscope according to the invention, especially a rectoscope, the hinge which connects the cover and the head housing is of releasable construction, not only can the cover be opened easily, but, if required, it can also be taken right off the head housing rapidly and in an uncomplicated manner. Neither during opening and closing, nor when the lid is removed or put on are there any jerky movements or torques which might hurt the patient.

A simple and particularly easily-operated construction for the hinge is obtained by having the hinge consist basically of an axial pin with an annular groove, the pin being adaptable to fit into a bore provided within a lug on the head housing. Within the lug there is a stop-ball projecting into the bore, loaded by means of a spring and engaging the annular pin groove when the axial pin is inserted in the bore.

It is most expedient for the lug to be attached to the housing of the head, preferably by means of a holding ring fixed to this, and for the axial pin to be attached to the cover. However, the arrangement may be switched, i.e., the pin may be integral with the housing, and the lug made part of the cover.

Preferably, there is a second bore in the lug, running transverse to the first bore provided therein, and serving to hold the spring and the stop-ball which moves in the second bore.

In another embodiment, a sleeve is provided within the first bore to receive the axial pin, which sleeve has a bore which lines up with the second bore and through which the stop-ball engages in the annular groove when the axial pin is inserted in the sleeve.

The stop-ball is suitably secured in a particularly simple way, but nonetheless very reliably, by means of an inwardly projecting burr provided at the end of the second bore.

So that the cover cannot fall shut from the open position when the rectoscope is being manipulated, preferably a third bore is provided, opening out in a face of the cover or the head housing opposite the axial pin, to house a spring and a stop-ball which projects into a recess in the head housing or in the cover when the cover is attached to the head in the open position.

The cover can be closed particularly rapidly, securely and leak-tight by means of attaching to the cover on the side opposite the hinge a screw which engages behind a chamfer on the head housing when the cover is closed.

BRIEF DESCRIPTION OF THE DRAWINGS

The invention is described in more detail with reference to the embodiment shown in the drawings, in which FIG. 1 shows a side view of the preferred embodiment;

FIG. 2 is a perspective view of the endoscope head, with the head housing and cover shown detached from each other;

FIG. 3 is an enlarged cross-section through the hinge which connects the head housing and the lug portion of the cover;

FIG. 4 is a side view of the head, with the cover open;

FIG. 5 is a side view of the head, with the cover closed; and

FIG. 6 is a cross-sectional view similar to FIG. 3, showing a sleeve in the lug bore.

DESCRIPTION OF THE PREFERRED EMBODIMENT

FIG. 1 shows the basic construction of a rectoscope 10 which consists substantially of a head 12 and a tube 14. There is a spacer sleeve 16 on the distal end of the tube 14. On the proximal end of the tube 14 there is a shield 18. Tube 14 is attached detachably or permanently to the head 12, of which the housing 20, a holding ring 24 attached thereto, a cover 26 hinged to housing 20, and a connecting fixture 22 and a screw 32 attached to the cover are illustrated. The connecting fixture 22 is used to attach a handle which is not shown, which either itself contains a lighting device or is connected to a cold light projector via a light-conducting cable. The light supplied from the handle is conducted from the connecting fixture 22 into the interior of the appliance via a bunch of light-conducting fibres. The exact construction of such a rectoscope is shown and described in detail in the German specification AS-PS No. 1 566 179 cited above, incorporated herein by reference.

FIG. 2 is a perspective view of the head 12 and part of tube 14 of the rectoscope 10, where the head housing and cover 26 are shown detached from each other. On one side of cover 26, being the upper side in FIG. 2, a seal 27 is attached. In a bore provided within the cover, a window 28 (a flat glass disc or lens through which observation is possible when the cover is closed) is installed by means of a holding ring 28'. A connecting fixture 29 is attached to the cover, and compressed air can be blown through such fixture into the inside of the rectoscope. Two diametrically opposed arms 43 and 44 are attached laterally to the cover 26. Arm 43 bears a radially adjustable screw 32, while on the arm 44 an axial pin 46 is attached. Pin 46 is dimensioned to fit in a bore 38 which is provided in a lug 36 attached to holding ring 24. Thus, when the axial pin 46 is inserted in the first bore 38, cover 26 can be pivoted around an axis perpendicular to the axis of the rectoscope. Thus, pin 46 in combination with bore 38 provide the means for opening and closing cover 26.

As is shown in more detail in FIG. 3, a second bore 40 is provided in lug 36 on the holding ring 24, bore 40 running perpendicular to the axis of first bore 38 and housing a compression spring 41 and a stop-ball 42 loaded thereby in the direction of first bore 38. The stop-ball 42 projects into the contour of the bore 38, so that when the axial pin 46 is inserted in the bore 38, the stop-ball engages in an annular groove 48 cut in the axial pin. Second bore 40, at its end which opens to first bore 38, has a burr 39 which can be punched in, for example, using a centre punch.

In practice, cover 26 is therefore easily detached from the housing 20 of the head 12, but on the other hand is held securely on it. The axial pin 46 and the bore 38 in the lug 36 thus form a releasable hinge 30.

Instead of the axial pin being inserted directly in the bore 38, having a bearing sleeve 56, shown in FIG. 6, can be inserted therein, having a bore the diameter of which is slightly smaller than that of the stop-ball 42, lining up with the second bore 40. When the axial pin 46 is inserted in the bearing sleeve, the stop-ball 42 then projects through the bore in the bearing sleeve into the annular groove 48. Referring to FIG. 4, located in the arm 44 of the cover 26 there is a third bore 50 made in the form of a blind hole, the open end of which opens out in the face of the cover 26 opposite the axial pin 46. The bore 50 houses a spring 52 and a stop-ball 54 which projects into a recess provided in the lug 36 when the cover 26 is in the open position. In this way the cover 26 is held securely in the open position without being able to swing shut accidentally as the endoscope is manipulated.

On the side of the holding ring 24 opposite the lug 36, a chamfer 35 is provided, sloping towards the distal end of the head 12 and towards its axis. Screw 32 is provided with a spherical end 34 which engages behind chamfer 35 when the cover 26 is closed, as shown in FIG. 5. In this way, good sealing is always obtained, even after the endoscope has been in use for a long time. The chamfer 35 has the additional advantage that compressed air inside the rectoscope 10 can escape only slowly when the cover 26 is opened, which prevents discomfort to the patient due to the sudden release of the compressed air. Thus, because of the engagement of the spherical end 34 and the chamfer 35 only a small slot is opened initially so that the pressure inside the rectoscope 10 escapes only slowly, instead of all at once as would happen with a sudden complete opening of cover 26.

While the invention has been disclosed particularly in the form of a rectoscope, it is to be understood that the releasable cover-housing head arrangement may be adapted for use with any other type of instrument. The important features are that the hinge pin be secured from accidental loosening when the cover is attached to the housing; that the hinge pin be easily released for detaching the cover from the housing (or that the cover be easily released from the pin if the pin is integral with the housing and the bore is in the cover); that the cover be held securely in the open position once it has been opened; and that the cover can be clamped closed onto the housing by means of the screw-chamfer arrangement. All of these features are adaptable to a cover/housing combination in any instrument environment, it being understood that the rectoscope as illustrated is a preferred embodiment but only one of many embodiments within the scope of the invention.

We claim:

1. An endoscope, especially a rectoscope, comprising a tube, a head housing and a detachable cover, said tube being connected to said head housing, said housing being adapted to be closed at the end opposite said tube by said cover, and releasable hinge means for attaching said cover to said housing, a lug attached to said housing and an axial pin attached to said cover, said hinge means comprising said axial pin with an annular groove, a first bore in said lug, a stop-ball mounted in projecting relation into said first bore, and spring means for loading said stop-ball to engage in said annular groove when said axial pin is inserted in said first bore.

2. The endoscope according to claim 1, comprising a second bore in said lug running transverse to said first bore for housing said spring means and said stop-ball, said second bore opening into said first bore.

3. The endoscope according to claim 1, in which a screw is provided on the side of said cover opposite said hinge means, said screw being adapted to engage behind a chamfer on said head housing when said cover is in its closed position.

4. The endoscope according to claim 2, further comprising a sleeve in said first bore to receive said axial pin, said sleeve having a transverse bore which lines up with said second bore and through which said stop-ball can project to engage in said annular groove when said axial pin is inserted in said sleeve.

5. The endoscope according to claim 2, wherein said second bore has a narrowing at said opening to a cross-sectional dimension less than the diameter of said stop-ball.

6. An endoscope, especially a rectoscope, comprising a tube, a head housing, and a detachable cover, said tube being connected to said head housing, said housing being adapted to be closed at the end opposite said tube by said cover, and releasable hinge means for attaching said cover to said housing, a lug attached to said housing and an axial pin attached to said cover, said hinge means comprising said axial pin with an annular groove, a first bore in said lug, a stop-ball mounted in projecting relation into said first bore, and spring means for loading said stop-ball to engage in said annular groove when said axial pin is inserted in said first bore, and further comprising a third bore provided to open out in the surface of the cover or of the head housing opposite to said axial pin, a second spring and second stop-ball being provided in said third bore, and a recess located in said head housing or cover so that said second stop-ball can project into said recess when said cover is attached to said head and is in its open position.

* * * * *